United States Patent
Choi et al.

(10) Patent No.: US 10,154,936 B2
(45) Date of Patent: Dec. 18, 2018

(54) CONNECTING MODULE AND MOTION ASSISTANCE APPARATUS INCLUDING THE SAME

(71) Applicant: Samsung Electronics Co., Ltd., Suwon-Si, Gyeonggi-Do (KR)

(72) Inventors: Byungjune Choi, Gunpo-si (KR); Youn Baek Lee, Yongin-si (KR); Se-gon Roh, Suwon-si (KR); Minhyung Lee, Anyang-si (KR); Jeonghun Kim, Hwaseong-si (KR); Jongwon Lee, Uiwang-si (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 81 days.

(21) Appl. No.: 14/536,964

(22) Filed: Nov. 10, 2014

(65) Prior Publication Data

US 2016/0016307 A1    Jan. 21, 2016

(30) Foreign Application Priority Data

Jul. 17, 2014    (KR) .......................... 10-2014-0090245

(51) Int. Cl.
*A61F 5/01* (2006.01)
*A61H 3/00* (2006.01)
(Continued)

(52) U.S. Cl.
CPC ............. *A61H 3/00* (2013.01); *A61H 1/0244* (2013.01); *F16H 7/04* (2013.01); *A61F 2/78* (2013.01); *A61F 5/01* (2013.01); *A61F 5/0102* (2013.01); *A61F 5/013* (2013.01); *A61F 5/0104* (2013.01); *A61F 5/0123* (2013.01); *A61F 5/0125* (2013.01); *A61F 5/0127* (2013.01); *A61F 5/0193* (2013.01); *A61F 2002/6836* (2013.01);
(Continued)

(58) Field of Classification Search
CPC ........................................................ A61F 2/78
See application file for complete search history.

(56) References Cited

U.S. PATENT DOCUMENTS 1,632,123 A * 6/1927 Witt .......................... F16H 1/46
475/296
1,764,314 A * 6/1930 Koch ........................ F16H 1/22
74/410
(Continued)

FOREIGN PATENT DOCUMENTS

JP     2012090849 A     5/2012
JP     2013059491 A     4/2013
(Continued)

*Primary Examiner* — Jacqueline Woznicki
(74) *Attorney, Agent, or Firm* — Harness, Dickey & Pierce, P.L.C.

(57) ABSTRACT

Provided are a connecting module and a motion assistance apparatus including the same, the connecting module including a case provided to incline downward from a space recessed between a waist and a hip of a user to a hip joint of the user, a power transmitting assembly disposed in an internal portion of the case, and a supporting module connecting portion disposed at an output terminal of the power transmitting assembly and to be fastened with a supporting module that supports a leg of the user.

19 Claims, 12 Drawing Sheets

(51) Int. Cl.
*A61H 1/02* (2006.01)
*F16H 7/04* (2006.01)
*A61F 2/68* (2006.01)
*A61F 2/78* (2006.01)
*F16H 1/22* (2006.01)
*F16H 1/20* (2006.01)

(52) U.S. Cl.
CPC . *A61F 2002/7862* (2013.01); *A61F 2005/016* (2013.01); *A61F 2005/0132* (2013.01); *A61F 2005/0134* (2013.01); *A61F 2005/0137* (2013.01); *A61F 2005/0139* (2013.01); *A61F 2005/0141* (2013.01); *A61F 2005/0144* (2013.01); *A61F 2005/0146* (2013.01); *A61F 2005/0148* (2013.01); *A61F 2005/0151* (2013.01); *A61F 2005/0153* (2013.01); *A61F 2005/0155* (2013.01); *A61F 2005/0158* (2013.01); *A61F 2005/0162* (2013.01); *A61F 2005/0165* (2013.01); *A61F 2005/0167* (2013.01); *A61F 2005/0169* (2013.01); *A61F 2005/0172* (2013.01); *A61F 2005/0174* (2013.01); *A61F 2005/0176* (2013.01); *A61F 2005/0179* (2013.01); *A61F 2005/0181* (2013.01); *A61F 2005/0183* (2013.01); *A61H 2201/1207* (2013.01); *A61H 2201/1238* (2013.01); *A61H 2201/1463* (2013.01); *A61H 2201/164* (2013.01); *A61H 2201/165* (2013.01); *A61H 2201/1628* (2013.01); *F16H 1/20* (2013.01); *F16H 1/203* (2013.01); *F16H 1/227* (2013.01)

(56) References Cited

U.S. PATENT DOCUMENTS

| | | | | |
|---|---|---|---|---|
| 2,299,268 A * | 10/1942 | Lloyd | A61B 17/1622 | 408/124 |
| 3,133,451 A * | 5/1964 | Thomas | F16H 1/22 | 74/410 |
| 3,845,668 A * | 11/1974 | Underwood | F16H 1/20 | 192/46 |
| 3,871,242 A * | 3/1975 | Linstromberg | F16D 11/00 | 74/421 A |
| 3,915,033 A * | 10/1975 | Polak | F16H 3/66 | 475/286 |
| 4,144,774 A * | 3/1979 | Berlinger, Jr. | F16H 19/001 | 251/249 |
| 4,503,731 A * | 3/1985 | Tomlinson | B65G 23/24 | 299/34.07 |
| 4,616,527 A * | 10/1986 | Frey | E05B 81/25 | 74/405 |
| 4,706,512 A * | 11/1987 | McKernon | E05B 81/25 | 292/336.3 |
| 4,823,632 A * | 4/1989 | Harrod | A63H 31/00 | 446/463 |
| 4,880,274 A * | 11/1989 | Ichikawa | B60N 2/2213 | 297/362 |
| 5,172,605 A * | 12/1992 | Schwartz | F16H 35/10 | 74/421 A |
| 5,282,460 A * | 2/1994 | Boldt | A61F 2/68 | 403/119 |
| 5,471,892 A * | 12/1995 | Sherman | F16H 3/093 | 475/207 |
| 5,830,168 A * | 11/1998 | Finnell | A61F 5/0193 | 602/23 |
| 5,954,621 A * | 9/1999 | Joutras | A43B 1/0054 | 482/114 |
| 5,980,435 A * | 11/1999 | Joutras | A43B 1/0054 | 482/114 |
| 6,227,073 B1 * | 5/2001 | Vilain | F16H 57/033 | 403/14 |
| 6,424,886 B1 * | 7/2002 | Iversen | A61F 2/54 | 403/128 |
| 6,601,467 B1 * | 8/2003 | Futterer | F16H 1/20 | 74/413 |
| 6,745,639 B2 * | 6/2004 | Nagai | F16H 1/20 | 74/420 |
| 6,857,338 B2 * | 2/2005 | Tsergas | F16H 57/028 | 74/421 A |
| 6,931,964 B2 * | 8/2005 | Thomas | B60K 17/344 | 74/413 |
| 7,168,336 B2 * | 1/2007 | Lin | G11B 17/028 | 74/406 |
| 7,191,678 B2 * | 3/2007 | Schunke | H02K 7/116 | 74/413 |
| 7,370,549 B2 * | 5/2008 | Haga | F16H 57/033 | 74/413 |
| 7,393,335 B2 * | 7/2008 | Carvey | A61F 5/0102 | 602/16 |
| 7,416,538 B2 | 8/2008 | Katoh et al. | | |
| 7,431,708 B2 * | 10/2008 | Sreeramagiri | A61F 5/0123 | 602/16 |
| 7,479,122 B2 * | 1/2009 | Ceriani | A61F 5/0123 | 602/16 |
| 7,628,766 B1 * | 12/2009 | Kazerooni | A61F 5/00 | 601/35 |
| 7,780,616 B2 | 8/2010 | Ketch et al. | | |
| 7,998,096 B1 | 8/2011 | Skoog | | |
| 8,221,339 B2 * | 7/2012 | Hirata | A61H 1/0244 | 601/34 |
| 8,303,525 B2 * | 11/2012 | Ikeuchi | A61H 3/008 | 482/66 |
| 8,313,448 B2 * | 11/2012 | Shimada | A61F 5/0102 | 600/595 |
| 8,424,406 B2 * | 4/2013 | Wintsch | F16H 35/00 | 74/421 A |
| 8,555,744 B2 * | 10/2013 | Hirooka | B25J 9/103 | 74/409 |
| 8,652,075 B2 | 2/2014 | Takahashi et al. | | |
| 8,657,772 B2 * | 2/2014 | Einarsson | A41D 13/1281 | 482/8 |
| 2001/0035062 A1 * | 11/2001 | Schutt | B60J 7/0573 | 74/413 |
| 2002/0059844 A1 * | 5/2002 | Leung | A63H 31/00 | 74/413 |
| 2003/0140717 A1 * | 7/2003 | Bennett | B60B 35/002 | 74/410 |
| 2005/0126323 A1 * | 6/2005 | Haga | F16D 1/0864 | 74/421 A |
| 2006/0178605 A1 * | 8/2006 | Sauber | A61F 5/0123 | 602/16 |
| 2006/0258967 A1 * | 11/2006 | Fujil | A61F 5/0102 | 602/23 |
| 2006/0264790 A1 * | 11/2006 | Kruijsen | A61F 5/0193 | 602/16 |
| 2007/0012131 A1 * | 1/2007 | Guo | F16H 35/10 | 74/413 |
| 2007/0056592 A1 * | 3/2007 | Angold | A61H 3/00 | 128/845 |
| 2009/0299243 A1 * | 12/2009 | Hirata | A61F 5/0193 | 602/23 |
| 2009/0306564 A1 * | 12/2009 | Hirata | A61F 5/0193 | 602/23 |
| 2010/0298746 A1 * | 11/2010 | Shimizu | A61H 3/008 | 601/35 |
| 2011/0024262 A1 * | 2/2011 | Nurnberg | B66B 23/026 | 198/330 |
| 2011/0066088 A1 * | 3/2011 | Little | B25J 9/0006 | 601/35 |
| 2011/0172570 A1 * | 7/2011 | Shimizu | A61H 1/0244 | 601/35 |
| 2011/0214524 A1 * | 9/2011 | Jacobsen | A61F 2/68 | 74/490.04 |
| 2011/0218466 A1 * | 9/2011 | Takahashi | A61H 1/0244 | 601/35 |
| 2011/0266323 A1 * | 11/2011 | Kazerooni | B25J 9/0006 | 224/575 |

(56) References Cited

U.S. PATENT DOCUMENTS

| | | | |
|---|---|---|---|
| 2012/0010749 A1* | 1/2012 | van der Merwe | A61F 2/54 700/264 |
| 2012/0157894 A1* | 6/2012 | Hiki | A61H 1/024 601/35 |
| 2012/0172770 A1* | 7/2012 | Almesfer | B25J 9/0006 601/35 |
| 2012/0271207 A1* | 10/2012 | Schoen | A61F 5/0102 601/34 |
| 2013/0104682 A1* | 5/2013 | Schneider | F16H 1/20 74/421 A |
| 2013/0138020 A1* | 5/2013 | Yasuhara | A61H 3/00 601/35 |
| 2013/0150980 A1* | 6/2013 | Swift | A61F 2/68 623/24 |
| 2013/0197408 A1* | 8/2013 | Goldfarb | A61F 5/0102 601/35 |
| 2013/0261513 A1* | 10/2013 | Goffer | B25J 9/0006 601/35 |
| 2013/0296746 A1* | 11/2013 | Herr | A61H 3/00 601/34 |
| 2013/0331744 A1* | 12/2013 | Kamon | A61H 3/00 601/35 |
| 2014/0012164 A1* | 1/2014 | Tanaka | B25J 9/0006 601/35 |
| 2014/0058299 A1* | 2/2014 | Sankai | A61B 5/112 601/35 |
| 2014/0276261 A1* | 9/2014 | Caires | A61H 1/024 601/33 |
| 2014/0276263 A1* | 9/2014 | Caires | A61H 3/00 601/34 |
| 2014/0276264 A1* | 9/2014 | Caires | A61H 3/00 601/34 |
| 2014/0276265 A1* | 9/2014 | Caires | A61H 3/00 601/34 |
| 2014/0296761 A1* | 10/2014 | Yamamoto | A61H 1/0244 602/23 |
| 2015/0190248 A1* | 7/2015 | Vitiello | A61F 2/60 623/24 |
| 2015/0190923 A1* | 7/2015 | Seo | B25J 9/0006 602/16 |
| 2015/0272809 A1* | 10/2015 | Accoto | A61H 1/0237 623/31 |
| 2015/0335514 A1* | 11/2015 | Choi | A61H 3/00 623/27 |
| 2015/0336265 A1* | 11/2015 | Choi | B25J 9/0006 414/4 |
| 2015/0366694 A1* | 12/2015 | Bujold | A61F 5/0102 602/16 |
| 2016/0016307 A1* | 1/2016 | Choi | A61H 3/00 74/423 |
| 2016/0030201 A1* | 2/2016 | Zoss | A61F 5/01 623/24 |
| 2016/0045387 A1* | 2/2016 | Lee | A61H 3/008 602/12 |
| 2016/0113831 A1* | 4/2016 | Hollander | A61H 1/0244 623/31 |
| 2016/0193102 A1* | 7/2016 | Roh | A61H 3/00 623/27 |
| 2017/0049659 A1* | 2/2017 | Farris | B25J 9/104 |
| 2017/0087716 A1* | 3/2017 | Bujold | B25J 9/0006 |

FOREIGN PATENT DOCUMENTS

| | | |
|---|---|---|
| KR | 100731899 B1 | 6/2007 |
| KR | 101040631 B1 | 6/2011 |
| KR | 101186540 | 9/2012 |
| KR | 20130111763 A | 10/2013 |

* cited by examiner

CONNECTING MODULE AND MOTION ASSISTANCE APPARATUS INCLUDING THE SAME

CROSS-REFERENCE TO RELATED APPLICATION

This application claims the priority benefit of Korean Patent Application No. 10-2014-0090245, filed on Jul. 17, 2014, in the Korean Intellectual Property Office, the entire disclosure of which is incorporated herein by reference.

BACKGROUND

1. Field

Example embodiments relate to a connecting module and/or a motion assistance apparatus including the same.

2. Description of the Related Art

With the onset of rapidly aging society, an increased number of people may experience inconvenience and agony from joint problems, and, therefore, an interest in a motion assistance apparatus that may help these people walk is growing. In addition, motion assistance apparatuses that may increase a muscular strength of a human body are being developed, for example, for military purposes.

In general, a motion assistance apparatus may include one or more of a body frame disposed on a trunk of a user, a pelvic frame coupled to a lower side of the body frame to cover a pelvis of the user, a femoral frame disposed on a thigh of the user, a sural frame disposed on a calf of the user, and a pedial frame disposed on a foot of the user. The pelvic frame and the femoral frame may be connected rotatably by a hip joint portion, the femoral frame and the sural frame may be connected rotatably by a knee joint portion, and the sural frame and the pedial frame may be connected rotatably by an ankle joint portion.

The motion assistance apparatus may include an active joint structure including a hydraulic system and/or a driving motor to drive each joint portion to improve a muscular strength of a leg of the user.

For example, a driving motor of a driving portion, a decelerator, and a frame of a fixing portion may be structurally connected to a joint portion in an axial direction.

SUMMARY

Some example embodiments relate to a connecting module.

In some example embodiments, the connecting module may include a case provided to incline downward from a space recessed between a waist and a hip of a user to a hip joint of the user, a power transmitting assembly disposed in an internal portion of the case, and a supporting module connecting portion disposed at an output terminal of the power transmitting assembly and to be fastened with a supporting module that supports a leg of the user.

The connecting module may further include a driving source provided at an input terminal of the power transmitting assembly and disposed in the recessed space.

The power transmitting assembly may include a plurality of decelerating gears disposed to incline downward in a longitudinal direction of the case.

The plurality of decelerating gears may include a first decelerating gear provided to receive a power from the driving source, and a second decelerating gear provided to receive a power from the first decelerating gear to rotate the supporting module connecting portion. The first decelerating gear and the second decelerating gear may respectively include a compound gear in which gears having different diameters are combined.

A gear having a relatively large diameter in the first decelerating gear may be connected to a driving gear of the driving source, a gear having a relatively small diameter in the first decelerating gear may be connected to a gear having a relatively large diameter in the second decelerating gear, and the gear having the relatively small diameter in the first decelerating gear and a gear having a relatively small diameter in the second decelerating gear may be disposed to face opposite sides.

The case may be provided to be bent, a gear having a relatively large diameter in the first decelerating gear may be connected to a driving gear of the driving source, a gear having a relatively small diameter in the first decelerating gear may be connected to a gear having a relatively large diameter in the second decelerating gear, and the gear having the relatively small diameter in the first decelerating gear and a gear having a relatively small diameter in the second decelerating gear may be disposed to face an identical side.

The case may be provided to be bent, and a driving gear of the driving source and at least a portion of the plurality of decelerating gears may correspond to bevel gears.

Widths of one end and another end of the case may be narrower than a width of a central portion of the case, and a diameter of a decelerating gear disposed at a center may be greater than a diameter of a decelerating gear disposed at the input terminal of the power transmitting assembly and a diameter of a decelerating gear disposed at the output terminal of the power transmitting assembly, among the plurality of decelerating gears.

The case may include a first case including a rigid material and provided to support the driving source, a second case including a rigid material and provided to support the supporting module connecting portion, and a third case including a flexible material and disposed between the first case and the second case.

The power transmitting assembly may include a longitudinal direction member provided to extend in a longitudinal direction of the third case.

The case may include a flexible frame including a flexible material, a driving source supporting portion provided on one side of the flexible frame to support the driving source, and a supporting module supporting portion provided on another side of the flexible frame to support the supporting module connecting portion.

The connecting module may further include a combining frame provided to cover at least a portion of a side surface of the waist of the user, and the case may be provided to be integrated with the combining frame.

Other example embodiments relate to a motion assistance apparatus.

In some example embodiments, the motion assistance apparatus may include a fixing member to be fixed to a part of a user, a supporting module to be fixed to another part of the user to assist a movement of the other part with respect to the part, and a connecting module including a driving source disposed on one side connected to the fixing member, a supporting module connecting portion disposed on another side connected to the supporting module, and a power transmitting assembly provided to transmit a power between the driving source and the supporting module connecting portion.

The connecting module may further include a case to be connected from a space recessed between a waist and a hip of the user to one of a plurality of joints of the user.

The power transmitting assembly may include a plurality of rotating bodies provided to transmit a power to each other, and the plurality of rotating bodies may be disposed to be aligned in a longitudinal direction of the case.

The connecting module may further include a combining frame provided to cover at least a portion of the part of the user, and the fixing member may be slidingly connected to the combining frame and adjustable based on a circumference of the user.

The driving source, the supporting module connecting portion, and the power transmitting assembly may be disposed in an internal portion of the combining frame.

The supporting module may be detachably provided on the connecting frame.

The supporting module connecting portion may include a connecting disc provided to rotate by a power received from the power transmitting assembly, the connecting disc may include a plurality of first combining portions provided to be mutually asymmetric based on an axis of rotation of the connecting disc, and the supporting module may include a plurality of second combining portions having shapes corresponding to shapes of the plurality of first combining portions.

The motion assistance apparatus may further include a joint member disposed between the supporting module connecting portion and the supporting module, and the joint member may be hinge-connected to the supporting module to enable the supporting module to freely perform an adduction or an abduction.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
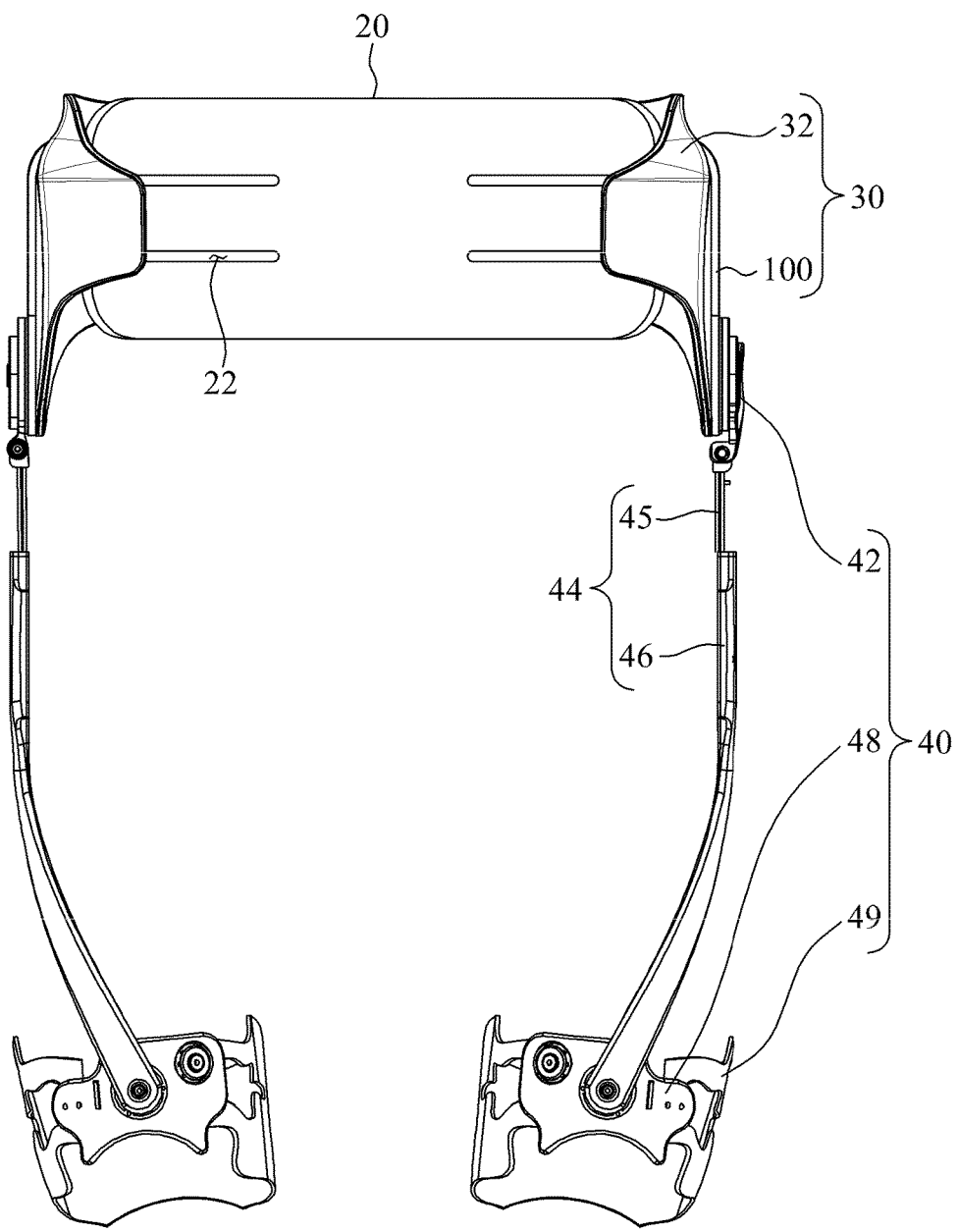
FIG. 1 is a front view illustrating a motion assistance apparatus according to some example embodiments.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

Figure 2:
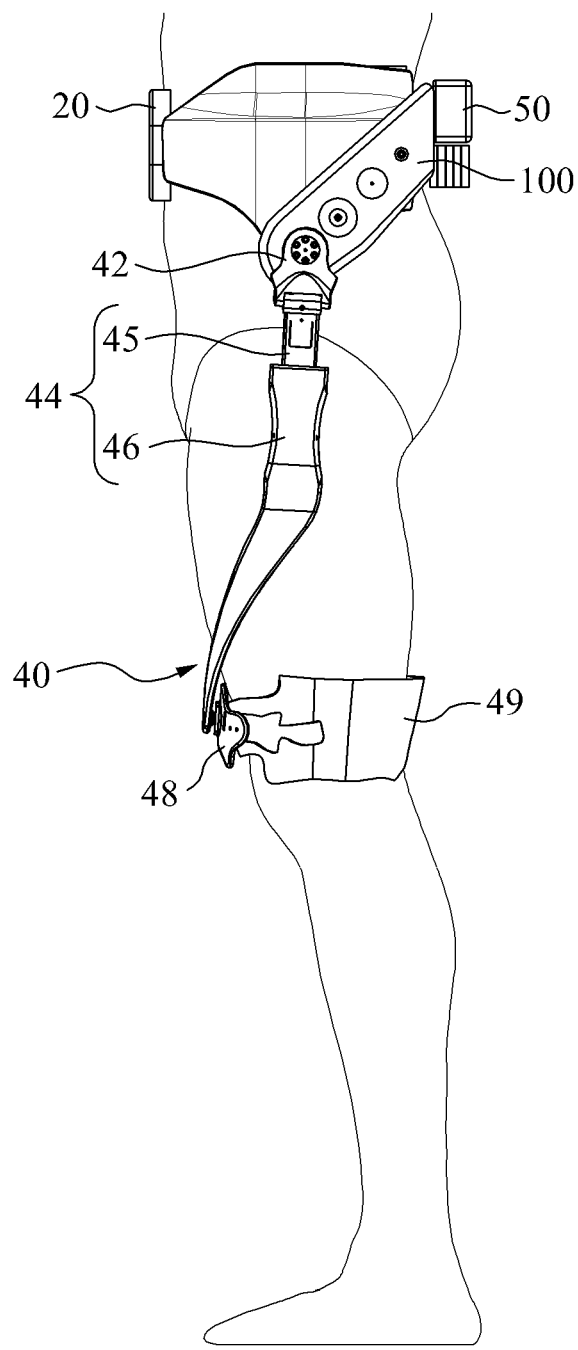
FIG. 2 is a side view illustrating a motion assistance apparatus according to some example embodiments.
Figure 3:
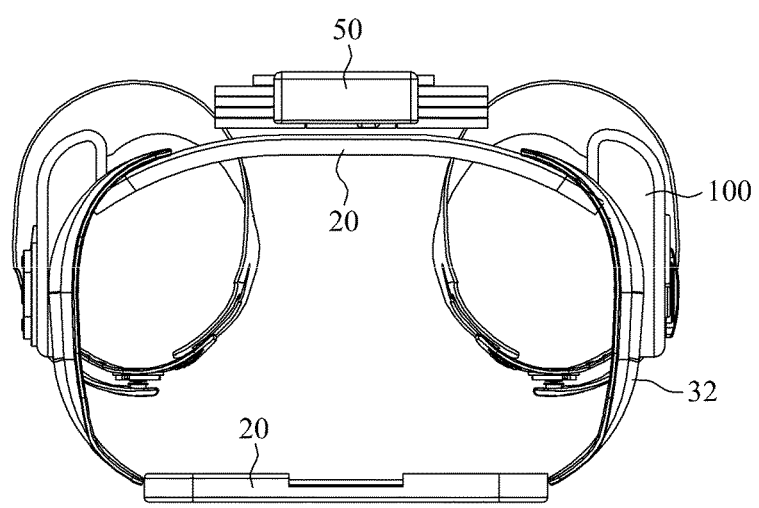
FIG. 3 is a top view illustrating a motion assistance apparatus according to some example embodiments.

FIG. 1 is a front view illustrating a motion assistance apparatus 10 according to some example embodiments, FIG. 2 is a side view illustrating the motion assistance apparatus 10 according to some example embodiments, and FIG. 3 is a top view illustrating the motion assistance apparatus 10 according to some example embodiments.

Referring to FIGS. 1 through 3, the motion assistance apparatus 10 may be worn on a user to assist a motion of the user.

The user may correspond to a human, an animal, or a robot, however, example embodiments are not limited thereto. In addition, although FIG. 1 illustrates a case in which the motion assistance apparatus 10 assists a motion of a thigh of the user, the motion assistance apparatus 10 may also assist a motion of another part of an upper body, for example, a hand, an upper arm, and a lower arm of the user, or a motion of another part of a lower body, for example, a foot, and a calf of the user. The motion assistance apparatus 10 may assist a motion of a part of the user.

Hereinafter, a case in which the motion assistance apparatus 10 assists a motion of a thigh of a human will be described.

The motion assistance apparatus 10 may include a fixing member 20, a connecting module 30, a supporting module 40, and a controller 50.

The fixing member 20 may be provided to cover at least a portion of a user. The fixing member 20 may be fixed to the user. The fixing member 20 may be in contact with at least a portion of an outer surface of the user. The fixing member 20 may be provided in a shape of covering at least a portion of the outer surface of the user. The fixing member 20 may be provided to be curved in a shape corresponding to the portion to be in contact with the user. The fixing member 20 may include a curved surface to be in contact with the user. For example, the fixing member 20 may be fixed to one side of a waist of the user. The fixing member 20 may be provided in a shape corresponding to a curve of a front surface or a rear surface of a waist of a human.

The fixing member 20 may include a flexible material. The fixing member 20 may be transformed to correspond to a shape of the outer surface of the user. For example, the fixing member 20 may include a fabric material or a synthetic resin material. The fixing member 20 may include an elastic material such as, for example, rubber and silicone.

The fixing member 20 may include a guide portion 22 to guide the connecting module 30.

The connecting module 30 may connect the fixing member 20 to the supporting module 40. The connecting module 30 may be detachable provided on the fixing member 20 and/or the supporting module 40. In some example embodiments, the connecting module 30 may be replaced based on a condition of the user. Conversely, the connecting module 30 may be used without being replaced, and the fixing member 20 and/or the supporting module 40 may be replaced.

The connecting module 30 may include a combining frame 32 and a connecting frame 100. The combining frame 32 and the connecting frame 100 may be provided as separate members, or provided integrally.

The combining frame 32 may be provided to cover at least a portion of the user. The combining frame 32 may be fixed to the user. The combining frame 32 may be in contact with at least a portion of the outer surface of the user. The combining frame 32 may be provided in a shape of covering at least a portion of the outer surface of the user. The combining frame 32 may be provided to be curved in a shape corresponding to the portion to be in contact with the user. The combining frame 32 may include a curved surface to be in contact with the user. For example, the combining frame 32 may be fixed to one side of the waist of the user. The combining frame 32 may be provided in a shape corresponding to a curve of a side surface of the waist of the human.

The combining frame 32 may include a flexible material. The combining frame 32 may be transformed to correspond to a shape of the outer surface of the user. For example, the combining frame 32 may include a fabric material or a synthetic resin material. The combining frame 32 may include an elastic material such as, for example, rubber and silicone.

The combining frame 32 may be connected to the fixing member 20 and the connecting frame 100. By means of the combining frame 32 and the fixing member 20, the motion assistance apparatus 10 may be fixed to a portion of the user. The combining frame 32 and the fixing member 20 may form a closed curved surface.

The combining frame 32 may be connected to the fixing member 20 to relatively move with respect to the fixing member 20. By relatively moving the combining frame 32 and the fixing member 20, the closed curved surface of the combining frame 32 and the fixing member 20 may be adjusted to correspond to the outer surface of the user. For example, the combining frame 32 may be slidingly connected to the guide portion 22 of the fixing member 20. The combining frame 32 may include a guide portion corresponding to the guide portion 22 of the fixing member 20. The guide portion 22 of the fixing member 20 may be provided to be recessed, and the guide portion of the combining frame 32 may be provided to protrude. Thus, the guide portion 22 of the fixing member 20 and the guide portion of the combining frame 32 may be coupled to each other.

The connecting frame 100 may provide a power to the supporting module 40. One side of the connecting frame 100 may be connected to the combining frame 32, and another side of the connecting frame 100 may be connected to the supporting module 40.

The connecting frame 100 may be disposed to incline downward with respect to the fixing member 20. For example, the one side of the connecting frame 100 may be disposed on a rear surface of the user, and the other side of the connecting frame 100 may be disposed on one side of a hip joint portion of the user.

The connecting frame 100 may extend from a space recessed on the outer surface of the user, and be connected to the supporting module 40. The recessed space on the outer surface of the user may be referred to as a "surplus space". The one side of the connecting frame 100 may be disposed in the surplus space. For example, the one side of the connecting frame 100 may be disposed on a rear side of the waist of the user. The one side of the connecting frame 100 may be disposed on an upper side of the hip of the user. The one side of the connecting frame 100 may be disposed on one side of a gluteus minimus of the user.

The connecting frame 100 may include a driving source, and power transmitting elements to transmit a power from the driving source to the supporting module 40. The connecting frame 100 will be further described in detail later.

The supporting module 40 may support a portion of the user. The supporting module 40 may assist a motion of the portion of the user. The supporting module 40 may move (e.g., rotate) by the power received from the connecting frame 100. A torque of the supporting module 40 may be transmitted to a portion of the user to assist a motion of the portion of the user.

The supporting module 40 may be detachably provided on the connecting frame 100. In some example embodiments, the supporting module 40 may be replaced based on a condition of the user.

The supporting module 40 may include a joint member 42, a supporting frame 44, a pressurizing member 48, and a supporting member 49.

The joint member 42 may transmit power between the connecting frame 100 and the supporting frame 44. One side of the joint member 42 may be connected to the connecting frame 100, and another side of the joint member 42 may be connected to the supporting frame 44.

The one side of the joint member 42 may be rotatably connected to an output terminal of the connecting frame 100. For example, the joint member 42 may be disposed on one side of a hip joint of the user. In this example, the joint member 42 may also be referred to as a "hip joint assistance member". The joint member 42 may be detachably provided on the connecting frame 100.

The other side of the joint member 42 may be hinge-connected to the supporting frame 44. The other side of the joint member 42 and the supporting frame 44 may be connected to each other in a hinge connection structure. A hinge axis of the hinge connection structure may intersect an axis of rotation of the joint member 42. For example, the hinge axis and the axis of rotation may be orthogonal to each other. The supporting frame 44 may perform a two degree of freedom (DOF) motion with respect to the fixing member 20 by means of the hinge axis and the axis of rotation.

A DOF may mean the number of independent motions of a mechanism, or the number of independent parameters that are required to specify an independent motion at a relative position with respect to links.

The joint member 42 may be detachably provided on the supporting frame 44. In this example, the joint member 42 may be a component of the connecting frame 100, and the supporting module 40 may be detachably provided on the joint member 42. The joint member 42 may be disposed between a supporting module connecting portion 140 (or, alternatively, a support connector 140) and the supporting module 40.

The joint member 42 may be hinge-connected to the supporting module 40 to enable the supporting module 40 to freely perform an adduction or an abduction. The joint member 42 may be a passive joint to prevent interference when the supporting frame 44 performs the adduction or the abduction in a direction orthogonal to a motion assistance direction of a portion of the user.

The supporting frame 44 may extend along a portion of the user. For example, the supporting frame 44 may extend in a longitudinal direction of the leg of the user. The supporting frame 44 may include a first supporting frame 45 connected to the joint member 42, and a second supporting frame 46 connected to the first supporting frame 45.

One side of the first supporting frame 45 may be connected to the joint member 42 by way of a hinge. Another side of the first supporting frame 45 may be connected to relatively move with respect to the second supporting frame 46. The first supporting frame 45 and the second supporting frame 46 may be connected to slidingly move. An overall length of the supporting frame 44 may be adjusted. In some example embodiments, the length of the supporting frame 44 may be adjusted based on a condition of the user. When the sliding structure of the first supporting frame 45 and the second supporting frame 46 is added, the supporting frame 44 may perform a three degree of freedom DOF motion with respect to the fixing member 20.

The pressurizing member 48 may be connected to one side of the second supporting frame 46. For example, the pressurizing member 48 may be disposed on one side of the leg of the user to push or pull the thigh of the user. The pressurizing member 48 may be disposed on a front surface of the thigh of the user.

The supporting member 49 may be connected to one side of the pressurizing member 48. For example, the supporting member 49 may be disposed to cover a circumference of at least a portion of the thigh of the user to prevent a separation of the thigh of the user from the supporting frame 44. The supporting member 49 may be disposed on an opposite side of the pressurizing member 48 with respect to the thigh of the user.

The controller 50 may control the connecting frame 100 to transmit a power to the supporting module 40. The controller 50 may be provided on one side of the fixing member 20. The controller 50 may be disposed in the surplus space of the user. For example, as shown in FIG. 2, the controller 50 may be provided on a rear side of the fixing member 20. The controller 50 may be disposed on a rear side of the waist of the user. The controller 50 may be disposed on an upper side of the hip of the user. However, a position of the controller 50 is not limited thereto.

The controller 50 may include a processor and a memory (not shown).

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the controller 200 as a special purpose computer to control the driving source 120, power transmitter 130 and/or the supporting module connection portion 140.

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

Figure 4:
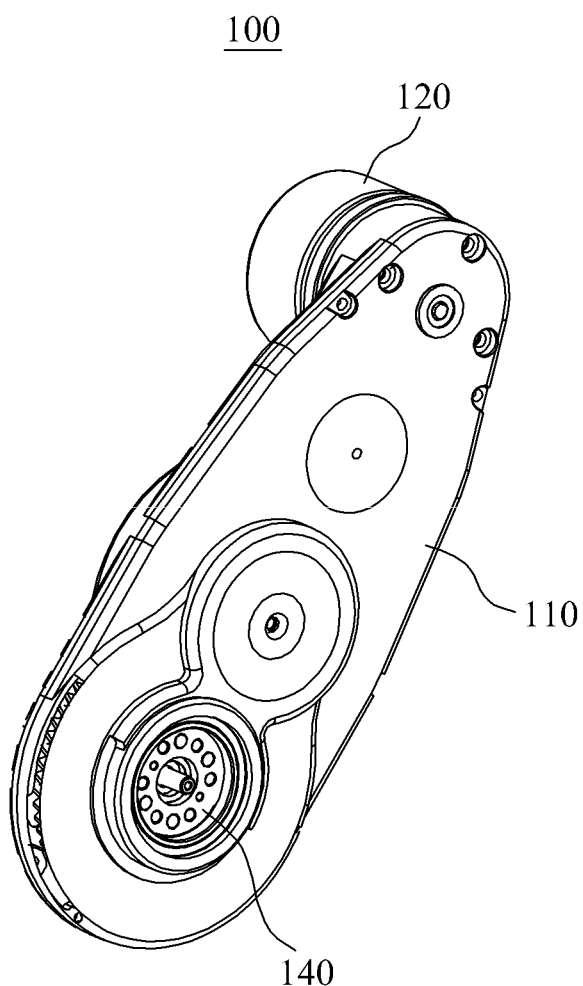
FIG. 4 is a perspective view illustrating a connecting frame according to some example embodiments.
Figure 5:
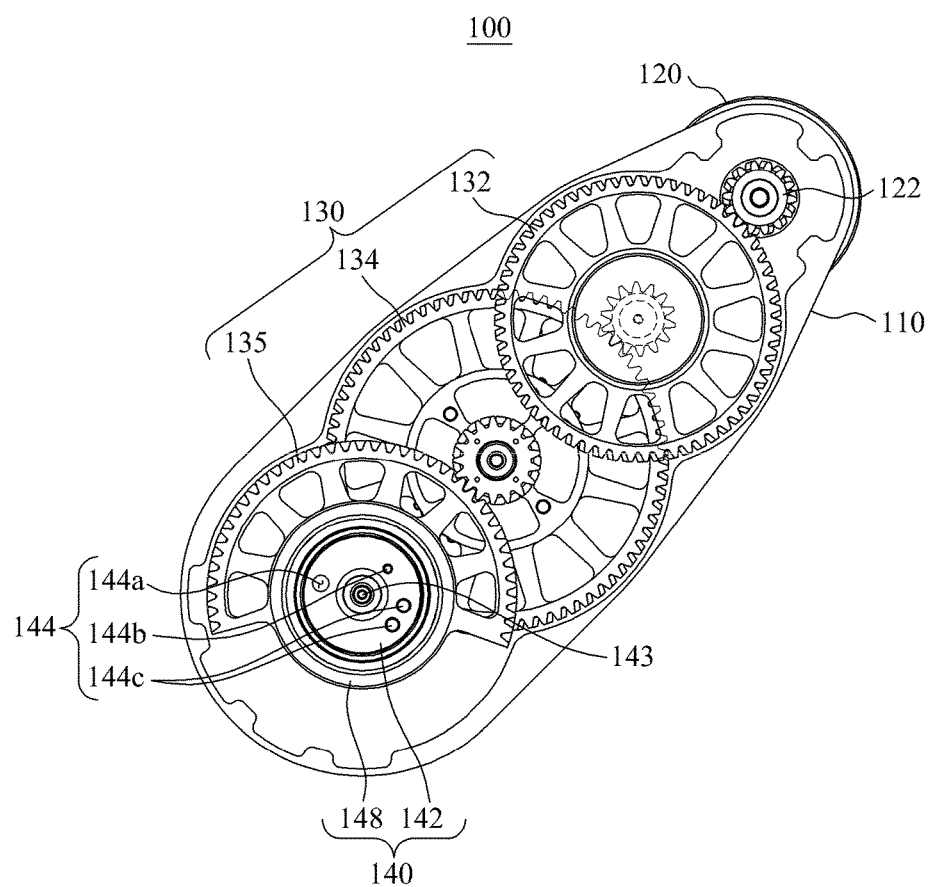
FIG. 5 is a cross-sectional side view illustrating a connecting frame according to some example embodiments.
Figure 6:
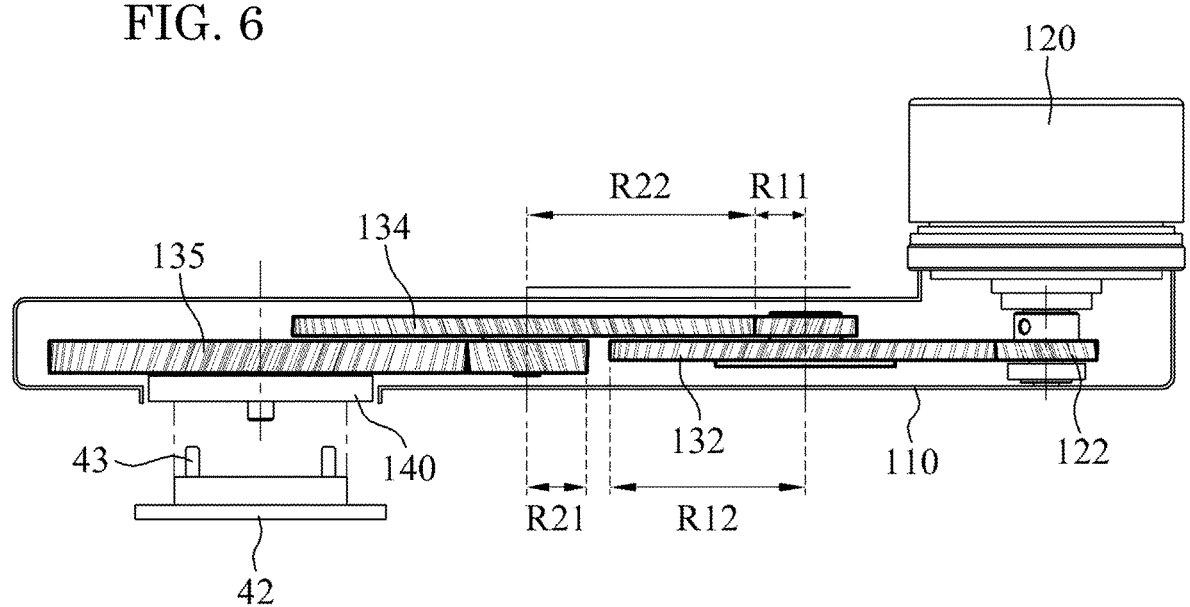
FIG. 6 is a cross-sectional top view illustrating a connecting frame according to some example embodiments.

FIG. 4 is a perspective view illustrating the connecting frame 100 according to some example embodiments, FIG. 5 is a cross-sectional side view illustrating the connecting frame 100 according to some example embodiments, and FIG. 6 is a cross-sectional top view illustrating the connecting frame 100 according to some example embodiments.

Referring to FIGS. 4 through 6, the connecting frame 100 may include a case 110, a driving source 120, a power transmitting assembly 130, and the supporting module connecting portion 140.

The case 110 may be formed to have a same shape as the connecting frame 100. One end of the case 110 may be connected to the driving source 120, and another side of the case 110 may be connected to the supporting module connecting portion 140. With respect to the case 110, the driving source 120 and the supporting module connecting portion 140 may be disposed in opposite directions. For example, the driving source 120 and the supporting module connecting portion 140 may be disposed to be spaced apart from each other.

The case 110 may be provided to cover the driving source 120, the power transmitting assembly 130, and at least a portion of the supporting module connecting portion 140. The case 110 may also be provided to completely cover the driving source 120. The case 110 may extend in a direction orthogonal to a driving axis of the driving source 120.

The case 110 may be provided to be integrated with the combining frame 32. An internal component of the case 110 may be provided in an internal portion of the combining frame 32. Through the above structure, a volume of the connecting module 30 may be reduced.

The driving source 120 may include, for example, a motor to receive a voltage or a current and to generate a power, and/or a driving source such as a pump operating by a fluid pressure. However, a type of the driving source 120 is not limited thereto. The driving source 120 may include a driving gear 122 to transmit a rotation power.

An overall thickness of the driving source 120 may be thicker than thicknesses of the power transmitting assembly 130 and the supporting module connecting portion 140. The driving source 120 may be disposed in the surplus space of the user. The driving source 120 may be provided in a size corresponding to a size of the surplus space. By disposing the driving source 120 in the surplus space, clothes protruding due to the driving source 120 when the user wears the motion assistance apparatus 10 with clothes may be prevented.

A body of the driving source 120 may be disposed in the surplus space, and the driving axis of the driving source 120 may be disposed to face an outer side surface of the user. For example, the driving axis of the driving source 120 may be disposed to be parallel to an axis of rotation of the hip joint of the user.

In other example embodiments, the driving source 120 may be completely covered by the case 110.

The power transmitting assembly 130 may transmit a power received from the driving gear 122 to the supporting module connecting portion 140. The power transmitting assembly 130 may include at least one decelerating gear. For example, the power transmitting assembly 130 includes a first decelerating gear 132, a second decelerating gear 134, and a third decelerating gear 135. Although FIG. 6 illustrates the power transmitting assembly 130 including three decelerating gears, a number of decelerating gears is not limited thereto.

The power transmitting assembly 130 may include a compound gear in which gears having different diameters are combined.

A gear having a relatively large diameter in the first decelerating gear 132 may be connected to the driving gear 122, and a gear having a relatively small diameter in the first decelerating gear 132 may be connected to the second decelerating gear 134.

A gear having a relatively large diameter in the second decelerating gear 134 may be connected to the first decelerating gear 132, and a gear having a relatively small diameter in the second decelerating gear 134 may be connected to the third decelerating gear 135.

The third decelerating gear 135 may be provided in a fan shape. A toothed gear may be provided on a portion of an outer circumferential surface of the third decelerating gear 135. In other words, the third decelerating gear 135 may include a toothed gear disposed at an angle corresponding to an angle at which the supporting module connecting portion 140 is rotatable. For example, the toothed gear of the third decelerating gear 135 may be disposed within a range between 180 degrees and 270 degrees. Through the above structure, a moment of rotation of the third decelerating gear 135 may be reduced and thus, a power transmission efficiency may increase.

In other example embodiments, the first decelerating gear 132 and the third decelerating gear 135 may be connected directly to each other, or a plurality of gears may be disposed between the first decelerating gear 132 and the third decelerating gear 135. The second decelerating gear 134 may commonly refer to one or more gears disposed between the first decelerating gear 132 and the third decelerating gear 135. Another power transmitting element may also be disposed between the first decelerating gear 132 and the third decelerating gear 135.

A maximum diameter of the first decelerating gear 132 may be smaller than a maximum diameter of the second decelerating gear 134. In this example, a width of one end portion of the case 110 may be reduced.

A sum of a diameter R11 of the gear having the relatively small diameter in the first decelerating gear 132 and a diameter R22 of the gear having the relatively large diameter in the second decelerating gear 134 may be greater than a sum of a diameter R12 of the gear having the relatively large diameter in the first decelerating gear 132 and a diameter R21 of the gear having the relatively small diameter in the second decelerating gear 134. In this example, as shown in FIG. 6, the gear having the relatively small diameter in the first decelerating gear 132 and the gear having the relatively small diameter in the second decelerating gear 134 may be disposed to face opposite sides. Through the above structure, a width of the case 110 may be relatively thin.

When a plurality of decelerating gears is disposed between the first decelerating gear 132 and the third decelerating gear 135, gears having relatively small diameters in a portion of the plurality of decelerating gears may be disposed to face opposite sides, similar to the first decelerating gear 132 and the second decelerating gear 134. Through the above structure, a width of the case 110 may be maintained to be relatively thin irrespective of a number of decelerating gears.

A maximum diameter of the third decelerating gear 135 may be smaller than the maximum diameter of the second decelerating gear 134. In this example, a width of another end portion of the case 110 may be reduced.

In the above configuration, as shown in FIG. 5, the case 110 may be provided in a shape in which a width of the case 110 decreases from a central portion of the case 110 toward both end sides of the case 110.

The supporting module connecting portion 140 may perform a single rigid body motion in conjunction with the third decelerating gear 135. The supporting module connecting portion 140 may be fastened to the third decelerating gear 135 through a separate fastening member, or provided to be integrated with the third decelerating gear 135. For example, the third decelerating gear 135 may be integrally provided on at least a portion of an edge portion of the supporting module connecting portion 140.

The supporting module 40 may be connected to the supporting module connecting portion 140. The supporting module 40 may be detachable from the supporting module connecting portion 140. For example, the supporting module 40 may be detachable in a lateral direction of the supporting module connecting portion 140. However, a direction in which the supporting module 40 is to be detached is not limited thereto.

The supporting module connecting portion 140 may include a connecting disc 142, and a connecting bearing 148.

The connecting disc 142 may perform a single rigid body motion in conjunction with the third decelerating gear 135. For example, the connecting disc 142 may be fastened to the third decelerating gear 135 through a separate fastening member, or provided to be integrated with the third decelerating gear 135. The connecting disc 142 may include an axis of rotation hole 143, and a first combining portion 144 including at least one hole.

An axis of rotation of the connecting disc 142 may be inserted into the axis of rotation hole 143.

Second combining portions 43 of the joint member 42 may be connected to the first combining portion 144. The at least one hole of the first combining portion 144 may be disposed to be asymmetric with respect to each other.

The first combining portion 144 may include a first hole 144a, a second hole 144b, and third holes 144c provided in the joint member 42. A diameter of the first hole 144a may be different from a diameter of the second hole 144b. Each of the first through third holes 144a to 144c may be one or more holes. A number of second holes 144b may be different from a number of third holes 144c. The second hole 144b and the third holes 144c may be disposed at different distances from a center of the axis of rotation hole 143.

Through the asymmetric disposition of the first combining portion 144, an improper combination of the joint member 42 may be prevented. The at least one hole of the first combining portion 144 may also be disposed to be symmetric with respect to each other.

The connecting bearing 148 may be disposed on one side of the connecting disc 142 to reduce a frictional force produced by rotation of the connecting disc 142 or the joint member 42. In an example, the connecting bearing 148 may be disposed between the connecting disc 142 and the case 110. In another example, the connecting bearing 148 may be disposed between the joint member 42 and the case 110.

Although the driving gear 122 and the decelerating gears 132, 134, and 135 corresponding to toothed gears are illustrated, example embodiments are not limited thereto. A gear may include a rotating body that may transmit a power by rolling friction.

Hereinafter, the same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 7:
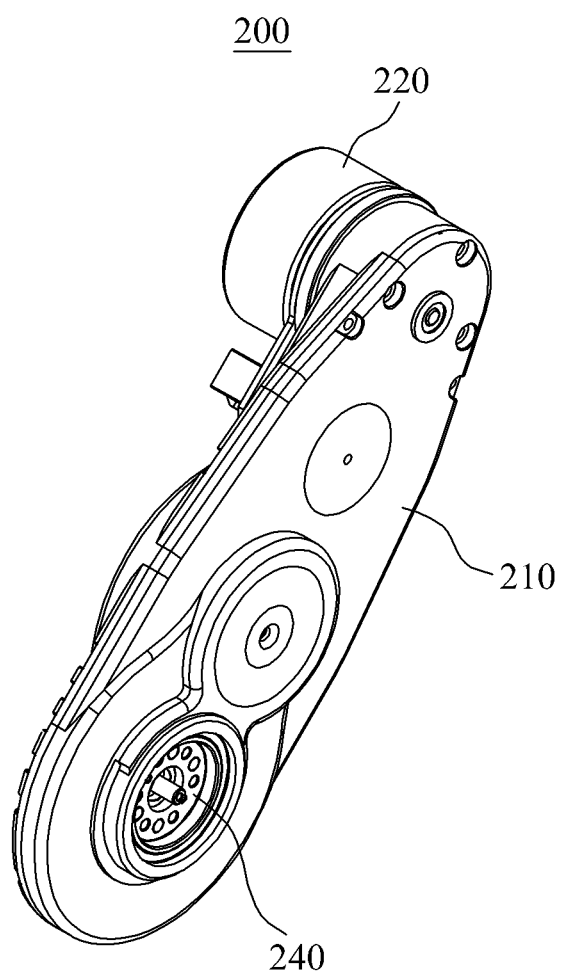
FIG. 7 is a perspective view illustrating a connecting frame according to some example embodiments.
Figure 8:
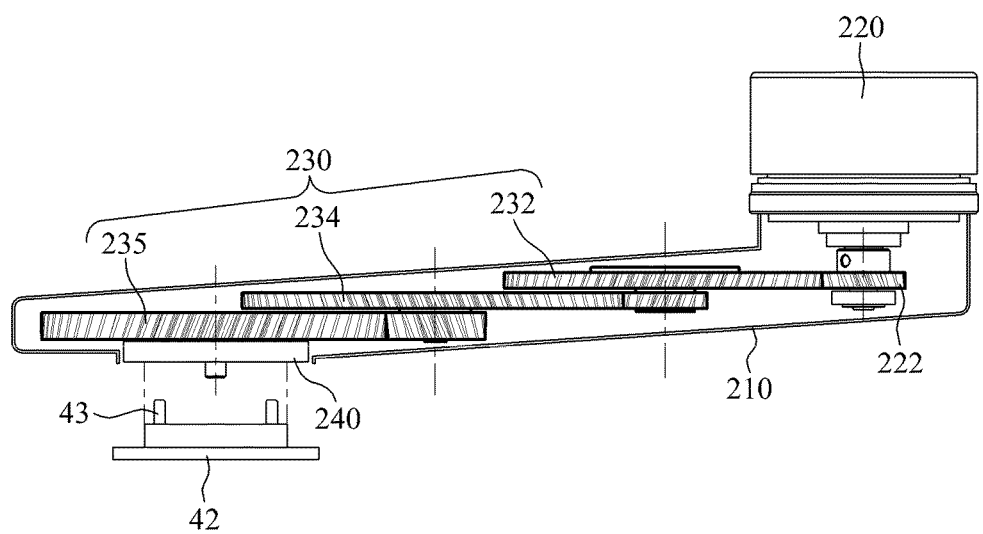
FIG. 8 is a cross-sectional top view illustrating a connecting frame according to some example embodiments.

FIG. 7 is a perspective view illustrating a connecting frame 200 according to other example embodiments, and FIG. 8 is a cross-sectional top view illustrating the connecting frame 200 according to other example embodiments.

Referring to FIGS. 7 and 8, the connecting frame 200 may include a case 210, a driving source 220, a power transmitting assembly 230, and a supporting module connecting portion 240.

The case 210 may extend in a direction orthogonal to a driving axis of the driving source 220. At least a portion of the case 210 may be provided to be bent. At least a portion of the case 210 disposed between the driving source 220 and the supporting module connecting portion 240 may be provided to incline. The case 210 may be provided to be bent from a rear portion of a user toward a front portion of the user. The case 210 may be provided to be bent along an outer surface of the user. Through the above structure, the case 210 may be in close contact with the user, and a height at which the entire connecting frame 100 externally protrudes may be reduced.

The case 210 may be provided to be bent in a shape identical to a shape of the outer surface of the user. The case 210 may be provided to be integrated with the combining frame 32. An internal component of the case 210 may be provided in an internal portion of the combining frame 32. Through the above structure, a volume of the connecting module 30 may be reduced.

The driving source 220 may include a driving gear 222. The power transmitting assembly 230 may include a first decelerating gear 232, a second decelerating gear 234, and a third decelerating gear 235.

As shown in FIG. 8, a gear having a relatively small diameter in the first decelerating gear 232 and a gear having a relatively small diameter in the second decelerating gear 234 may be disposed to face an identical side. Through the above structure, the case 210 may be provided in a bent shape. Although FIG. 8 illustrates the case 210 provided to incline at a particular angle, the case 210 may be provided to incline at various angles.

When a plurality of decelerating gears is disposed between the first decelerating gear 232 and the third decelerating gear 235, gears having relatively small diameters in a portion of the plurality of decelerating gears may be disposed to face an identical side, similar to the first decelerating gear 232 and the second decelerating gear 234. Through the above structure, the case 210 may be provided in a shape of being bent at various angles, as necessary. As shown in FIGS. 5 and 6, the decelerating gears 232, 234, and 235 may be combined and disposed along with decelerating gears including gears having relatively small diameters disposed to face opposite sides.

Figure 9:
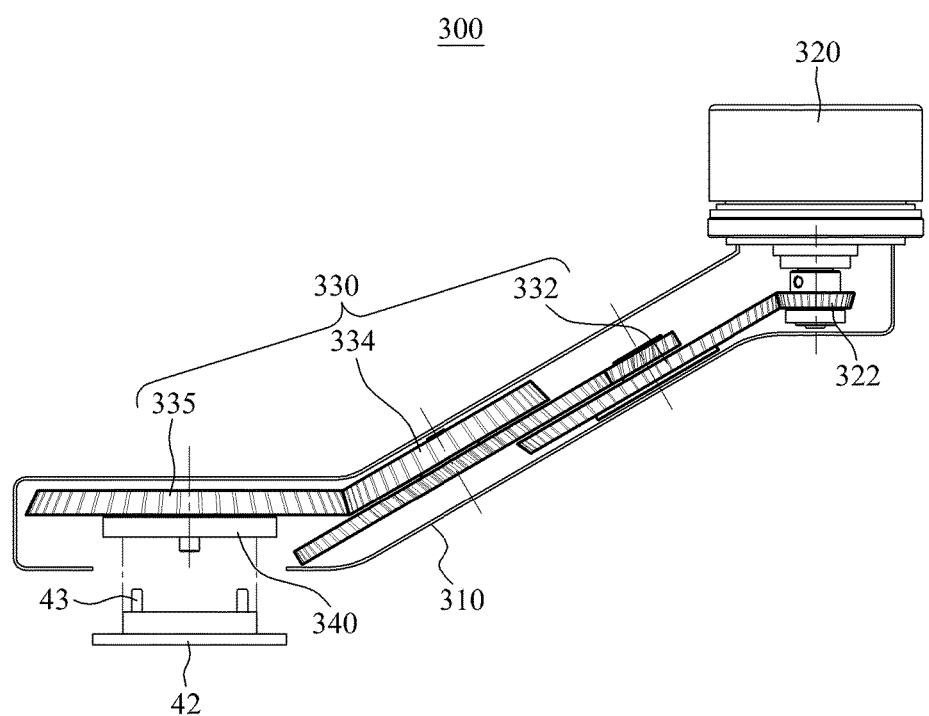
FIG. 9 is a cross-sectional top view illustrating a connecting frame according to some example embodiments.

FIG. 9 is a cross-sectional top view illustrating a connecting frame 300 according to other example embodiments.

Referring to FIG. 9, the connecting frame 300 may include a case 310, a driving source 320, a power transmitting assembly 330, and a supporting module connecting portion 340.

The driving source 320 may include a driving gear 322. The power transmitting assembly 330 includes a first decelerating gear 332, a second decelerating gear 334, and a third decelerating gear 335.

A gear having a relatively large diameter in the second decelerating gear 334 may be disposed on an outer side of a bending direction of the case 310, and a gear having a relatively small diameter in the second decelerating gear 334 may be disposed on an inner side of the bending direction of the case 310.

A portion of the driving gear 322 and the decelerating gears 332, 334, and 335 may be provided to incline. The portion of the driving gear 322 and the decelerating gears 332, 334, and 335 may be a bevel gear. Through the above structure, a connecting frame 300 having a speed reduction ratio as shown in FIG. 8 and an overall shape of being more greatly bent may be provided.

Figure 10:
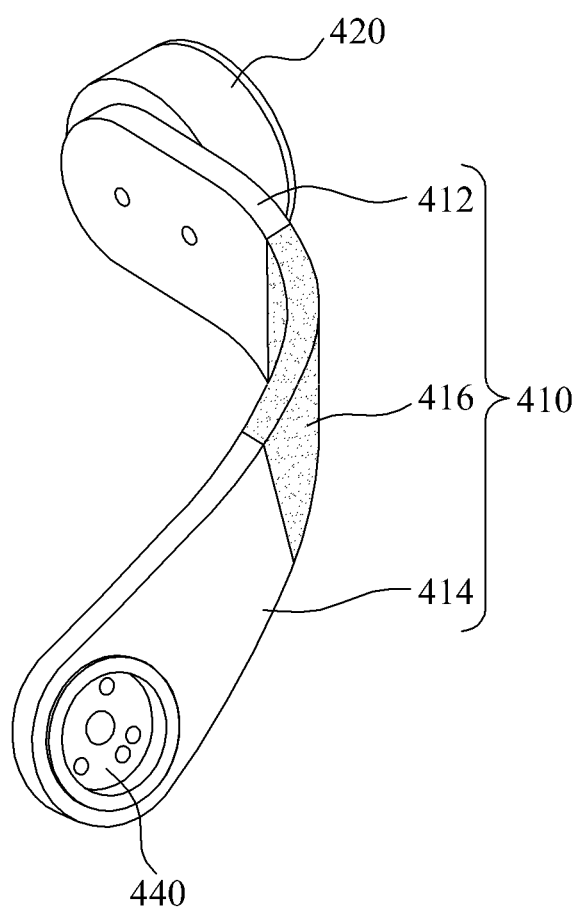
FIG. 10 is a perspective view illustrating a connecting frame according to some example embodiments.
Figure 11:
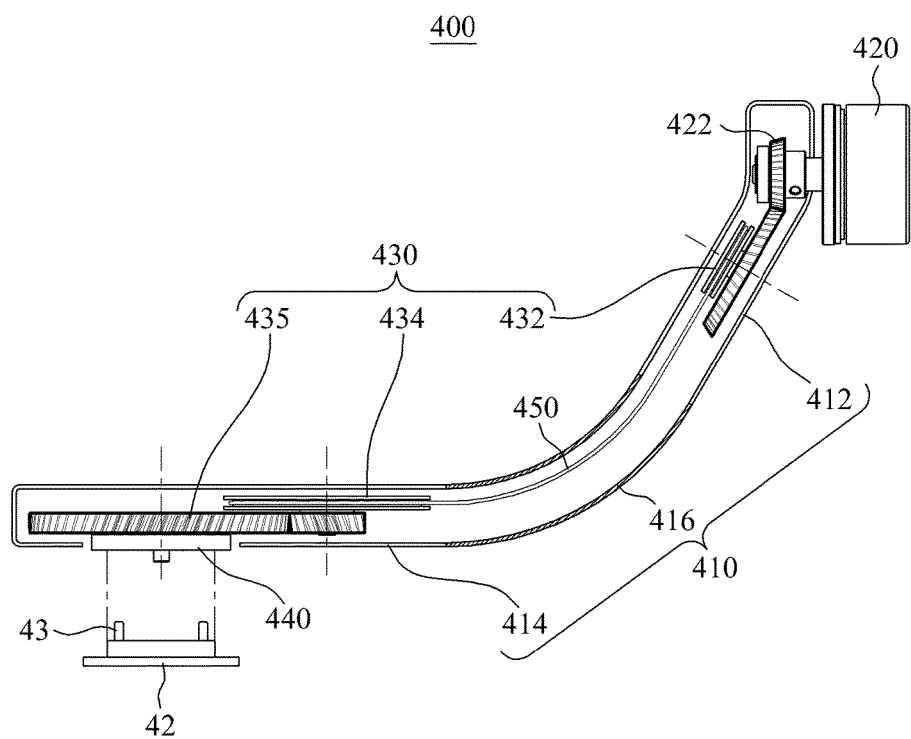
FIG. 11 is a cross-sectional top view illustrating a connecting frame according to some example embodiments.

FIG. 10 is a perspective view illustrating a connecting frame 400 according to other example embodiments, and FIG. 11 is a cross-sectional top view illustrating the connecting frame 400 according to other example embodiments.

Referring to FIGS. 10 and 11, the connecting frame 400 may include a case 410, a driving source 420, a power transmitting assembly 430, and a supporting module connecting portion 440.

The case 410 may be transformed to correspond to a shape of an outer surface of a user. The case 410 may include a flexible material. The case 410 may include a first case 412 disposed at one end of the case 410, a second case 414 disposed at another end of the case 410, and a third case 416 disposed at a central portion of the case 410.

The first case 412 may be disposed on a side surface and/or a rear surface of the user. The second case 414 may be disposed on one side of a hip joint of the user. The first case 412 and the second case 414 may respectively include a rigid material.

The first case 412 may be disposed on one side of the driving source 420. In this example, the first case 412 may also be referred to as a "driving source supporting case".

The second case 414 may be disposed on one side of the supporting module connecting portion 440. In this example, the second case 414 may also be referred to as a "supporting module supporting case".

The third case 416 may connect the first case 412 to the second case 414. The third case 416 may include a flexible material. The third case 416 may also be referred to as a "flexible case".

The driving source 420 may include a driving gear 422. The driving source 420 may be supported by the first case 412. Since the first case 412 includes a rigid material, the driving source 420 may be stably supported.

A body of the driving source 420 may be disposed in a surplus space, and a driving axis of the driving source 420 may be disposed to face a surface of the user. For example, the driving axis of the driving source 420 may be disposed in a direction intersecting an axis of rotation of the hip joint of the user.

The power transmitting assembly 430 includes a first decelerating gear 432, a second decelerating gear 434, a third decelerating gear 435, and a power transmitting member 450.

The first decelerating gear 432 may be supported by the first case 412. Since the first case 412 includes a rigid material, a relative distance between the driving gear 422 and the first decelerating gear 432 may be maintained. A gap to be provided between the driving gear 422 and the first decelerating gear 432 may be prevented.

The second decelerating gear 434 and/or the third decelerating gear 435 may be supported by the second case 414. Since the second case 414 includes a rigid material, the second decelerating gear 434 and/or the third decelerating gear 435 may be stably supported. In addition, a relatively distance between the second decelerating gear 434 and the third decelerating gear 435 may be maintained. Thus, a gap to be provided between the second decelerating gear 434 and the third decelerating gear 435 may be prevented The power transmitting member 450 may be disposed on an inner side of the third case 416. The power transmitting member 450 may be disposed between the driving source 420 and the supporting module connecting portion 440 to transmit a power. The power transmitting member 450 may be connected to two of the driving gear 422, the first decelerating gear 432, the second decelerating gear 434, and the third decelerating gear 435 to transmit a power. The power transmitting member 450 may be connected between a gear having a relatively small diameter in the first decelerating gear 432 and a gear having a relatively large diameter in the second decelerating gear 434 to transmit a power.

The power transmitting member 450 may include a longitudinal direction member extending in a longitudinal direction of the third case 416. The power transmitting member 450 may include a wire, a cable, a string, a link, a rubber band, a spring, a belt, and a chain. The power transmitting member 450 may include an elastic material. In this example, although the case 410 is transformed, the power may be stably transmitted without being lost.

Figure 12:
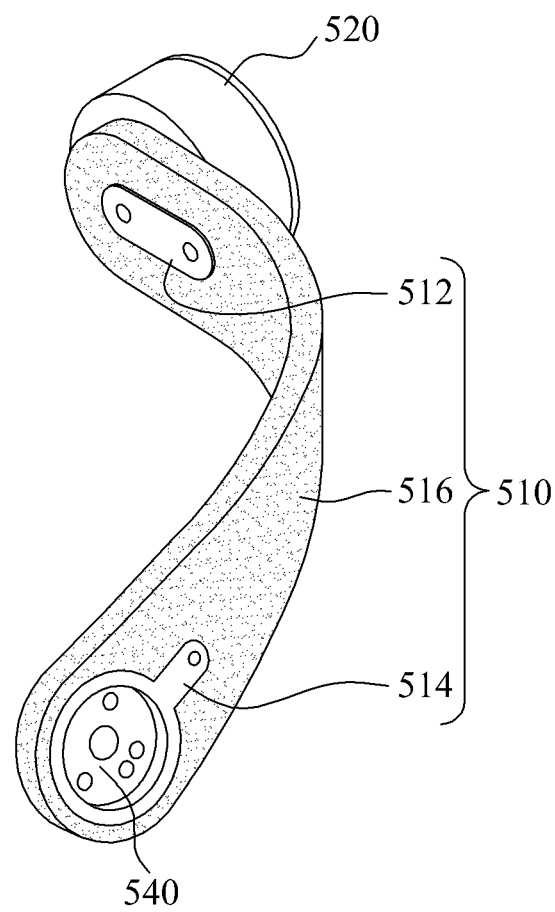
FIG. 12 is a perspective view illustrating a connecting frame according to some example embodiments.

FIG. 12 is a perspective view illustrating a connecting frame 500 according to other example embodiments.

Referring to FIG. 12, the connecting frame 500 may include a case 510, a driving source 520, a power transmitting assembly (not shown), and a supporting module connecting portion 540.

The case 510 may be transformed to correspond to a shape of an outer surface of a user. The case 510 includes a flexible frame 516 including a flexible material, a driving source supporting portion 512 provided on one side of the flexible frame 516, and a supporting module supporting portion 514 provided on another side of the flexible frame 516.

The driving source supporting portion 512 may be disposed on one side of the driving source 520. The driving source supporting portion 512 may connect a driving axis of the driving source 520 to the axis of rotation of the first decelerating gear 432 of FIG. 11.

The supporting module supporting portion 514 may be disposed on one side of the supporting module connecting portion 540. The supporting module supporting portion 514 may connect the axis of rotation of the second decelerating gear 434 of FIG. 11 to the axis of rotation of the third decelerating gear 435 of FIG. 11.

A number of example embodiments have been described above. Nevertheless, it should be understood that various modifications may be made to these example embodiments without departing from the scope of the disclosure. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A connecting module comprising:
a combining frame including a side cover to cover at least a gluteus minimus of a user and a hip joint cover extended downward from the side cover to cover a hip joint of the user;
a connecting frame fixed to the combining frame;
a driving source originating and projecting axially from a first side of the connecting frame and extending in a first direction from a rear portion of the side cover of the combining frame towards the user such that at least a portion of the driving source is disposed in a recessed space between a waist and the hip joint of the user and spaced away from the hip joint;
a support connector originating and projecting axially from a second side of the connecting frame and extending in a second direction from the hip joint cover of the combining frame away from the user at a position on the connecting frame eccentric from the driving source such that a driving axis of the driving source is eccentric to an axis of rotation of the support connector with respect to the combining frame, the axis of rotation of the support connector being rotationally controlled by the driving source, the second direction being opposite the first direction, the support connector configured to connect with a support that directly supports a thigh of the user; and
a power transmitting assembly configured to transfer driving power from the driving source to the support connector.

2. The connecting module of claim 1, wherein the power transmitting assembly comprises:
a plurality of decelerating gears incline downward in a diagonal direction from the driving source to the support connector.

3. The connecting module of claim 2, wherein the plurality of decelerating gears comprises:
a first compound gear assembly, a second compound gear assembly and a third compound gear assembly therebetween, each of the first compound gear assembly, the second compound gear assembly and the third compound gear assembly including a large gear and a small gear sharing a same axis such that, when the large gear of the first compound gear assembly receives power, the small gear of the first compound gear assembly meshes with teeth of the large gear of the third compound gear assembly, wherein
the first compound gear assembly is configured to receive a power from the driving source,
the third compound gear assembly is configured to receive a power from the first compound gear assembly to rotate the support connector.

4. The connecting module of claim 3, wherein
the small gear of the first compound gear assembly and the small gear of the third compound gear assembly face opposite sides of a case associated with the connecting frame.

5. The connecting module of claim 3, wherein
the connecting frame includes a case, the case being bent,
the large gear of the first compound gear assembly is configured to connect to a driving gear of the driving source,
the small gear of the first compound gear assembly is configured to connect to the large gear of the second compound gear assembly, and
the small gear of the first compound gear assembly and the small gear of the second compound gear assembly are disposed to face a same side of the case.

6. The connecting module of claim 3, further comprising:
a case configured to cover the power transmitting assembly, wherein
a diameter of the large gear of the third compound gear assembly at a central portion is greater than a diameter of the large gear of the first compound gear assembly at an input terminal of the power transmitting assembly and a diameter of the large gear of the second compound gear assembly at an output terminal of the power transmitting assembly such that widths of end portions of the case are narrower than a width of the central portion of the case.

7. The connecting module of claim 2, wherein
the connecting frame includes a case, the case is being bent, and
a driving gear of the driving source and at least a portion of the plurality of decelerating gears are bevel gears.

8. The connecting module of claim 1, wherein the connecting frame includes a case, the case comprising:
a first case connected to the driving source, the first case including a rigid material such that the first case is configured to support the driving source;
a second case connected to the support connector, the second case including a rigid material such that the second case is configured to support the support connector; and
a third case connected between the first case and the second case, the third case including a flexible material.

9. The connecting module of claim 8, wherein the power transmitting assembly comprises:
a longitudinal direction member configured to extend in a longitudinal direction of the third case.

10. The connecting module of claim 1, wherein the connecting frame includes a case, the case comprising:
a flexible frame including a flexible material;
a driving source support on one side of the flexible frame, the driving source support configured to support the driving source; and
a support connector support provided on another side of the flexible frame, the support connector support configured to support the support connector.

11. The connecting module of claim 1, further comprising:
a case configured to cover the power transmitting assembly, wherein the case is configured to integrate with the combining frame.

12. The connecting module of claim 1, wherein
the power transmitting assembly has a plurality of gears,
the driving axis of the driving source is eccentric to the axis of rotation of the support connector that is connected to the driving source via the plurality of gears, and
the power transmitting assembly is configured to transfer driving power from the driving source to the support connector via the plurality of gears.

13. A motion assistance apparatus comprising:
a fixing member configured to attach to a waist of a user;
a support configured to be fixed to a thigh of the user to assist a movement of the thigh; and
a connecting module including,
a combining frame including a side cover configured to cover at least a glutueus minimus of the user and a hip joint cover extended downward from the side cover to cover a hip joint of the user,
a connecting frame fixed to the combining frame, the connecting frame configured to transmit power to the support,
a driving source originating and projecting axially from a first side of the connecting frame and extending in a first direction from a rear portion of the side cover of the combining frame towards the user such that at least a portion of the driving source is disposed in a recessed space between the waist and a hip joint of the user and spaced away from the hip joint,
a support connector originating and projecting axially from a second side of the connecting frame and extending in a second direction from the hip joint cover of the combining frame away from the user at a position on the connecting frame eccentric from the driving source such that a driving axis of the driving source is eccentric to an axis of rotation of the support connector with respect to the combining frame, the axis of rotation of the support connecting being rotationally controlled by the driving source, the second direction being opposite the first direction, the support connector configured to connect with the support that directly supports the thigh of the user,
a power transmitting assembly configured to transmit the power from the driving source to the support connector, and
a case configured to mount in a space recessed between a waist and a hip of the user such that the case is-configured to incline downward the hip of the user.

14. The motion assistance apparatus of claim 13, wherein the power transmitting assembly comprises
a plurality of rotating bodies provided to transmit the power therebetween, the plurality of rotating bodies are configured to align in a longitudinal direction of the case.

15. The motion assistance apparatus of claim 13, wherein the combining frame is configured to slidably connect to the fixing member such that the combining frame is adjustable based on a circumference of the waist of the user.

16. The motion assistance apparatus of claim 15, wherein the driving source, the support connector, and the power transmitting assembly are inside the combining frame.

17. The motion assistance apparatus of claim 13, wherein the support is configured to detach from the connecting frame.

18. The motion assistance apparatus of claim 17, wherein the support connector comprises:
a connecting disc configured to rotate in response to a power received from the power transmitting assembly, the connecting disc including a plurality of first combining portions provided to be mutually asymmetric based on an axis of rotation of the connecting disc, wherein
the support includes a plurality of second combining portions having shapes corresponding to shapes of the plurality of first combining portions.

19. The motion assistance apparatus of claim 13, further comprising:
a joint member between the support connector and the support, the joint member including a hinge configured to connect the connecting frame and the support such that the support can adduct and abduct.

* * * * *